United States Patent [19]

Szantay et al.

[11] 4,314,939
[45] Feb. 9, 1982

[54] PROCESS FOR THE PREPARATION OF 15-HYDROXYIMINO-E-HOMOEBURNANE AND INTERMEDIATES THEREFOR

[75] Inventors: Csaba Szántay; Lajos Szabo; György Kalaus; Lajos Dancsi; Tibor Keve; Ferenc Drexler, all of Budapest, Hungary

[73] Assignee: Richter Gedeon Vegyészeti Gyár Rt., Budapest, Hungary

[21] Appl. No.: 168,560

[22] Filed: Jul. 14, 1980

[30] Foreign Application Priority Data

Jul. 13, 1979 [HU] Hungary .............................. RI 719

[51] Int. Cl.³ .................... C07D 471/22; A61K 31/55
[52] U.S. Cl. .......................... 260/239.3 P; 260/244.4; 424/256
[58] Field of Search ...................... 260/239.3 P, 244.4

[56] References Cited

PUBLICATIONS

Laronze et al., "Bulletin de la Societe Chimique de France", (1977), Nos. 11–12, pp. 1207–1214.

Primary Examiner—Robert T. Bond
Attorney, Agent, or Firm—Karl F. Ross

[57] ABSTRACT

A process for the preparation of 15-hydroxyimino-E-homoeburnane derivatives of the formula (I),

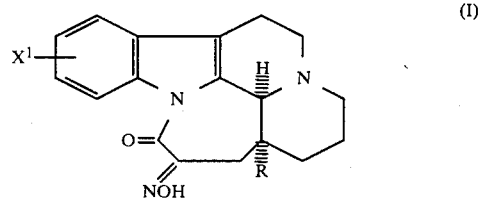

(I)

wherein

X¹ stands for hydrogen or halogen and
R is a $C_{1-6}$ alkyl group, or acid addition salts and optically active derivatives thereof. These compounds are valuable intermediates of the synthesis of compounds with outstanding biological effects. According to the invention a racemic or optically active 15-hydroxy-E-homoeburnane derivative of the formula (II),

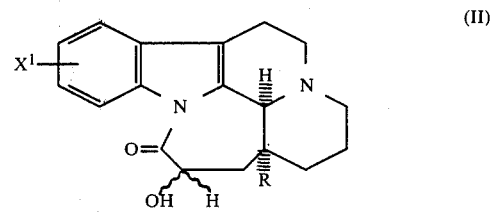

(II)

is treated, optionally after separating the 15-epimers and/or resolution, with a halogenating agent. The resulting 15-halo-E-homoeburnane derivative of the formula (III),

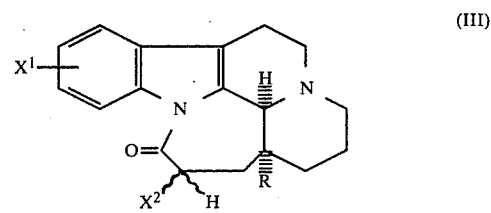

(III)

wherein X² stands for halogen, is reacted, optionally after separating the 15 epimers and/or resolution, with an alkali nitrite in the presence of an acid, and, if desired, the resulting 15-hydroxyimino-E-homoeburnane derivative of the formula (I) is converted into its acid addition salt and/or resolved. The compounds of the formula (III) formed as intermediates in the above process are new and biologically active.

27 Claims, No Drawings

PROCESS FOR THE PREPARATION OF 15-HYDROXYIMINO-E-HOMOEBURNANE AND INTERMEDIATES THEREFOR

The invention relates to a new process for the preparation of 15-hydroxyimino-E-homoeburnane derivatives of the formula (I),

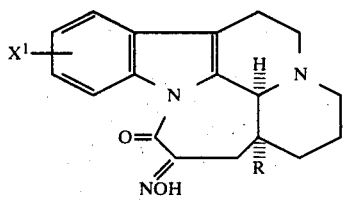

(I)

wherein
$X^1$ is hydrogen or halogen and
R is a $C_{1-6}$ alkyl group, and acid addition salts and optically active derivatives thereof.

According to the invention a racemic or optically active 15-hydroxy-E-homoeburnane derivative of the formula (II),

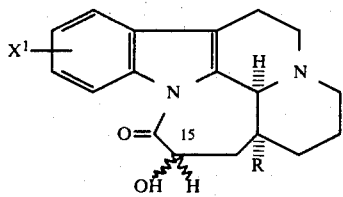

(II)

wherein R and $X^1$ are as defined above, is treated, optionally after separating the 15-epimers and/or resolution, with a halogenating agent, the resulting 15-halo-E-homoeburnane derivative of the formula (III),

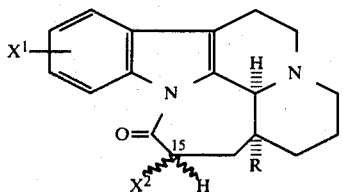

(III)

wherein R and $X^1$ are as defined above and $X^2$ stands for halogen, is reacted, optionally after separating the 15-epimers and/or resolution, with an alkali nitrite in the presence of an acid, and, if desired, the resulting 15-hyroxyimino-E-homoeburnane derivative of the formula (I) is converted into its acid addition salt and/or resolved.

The compounds of the formula (I) are valuable intermediates applicable in the preparation of compounds with outstanding pharmacological effects, such as apovincaminic acid ethyl ester, vincamine, 11-bromovincamine, etc. Thus the compounds of the formula (I) in which $X^1$ stands for hydrogen and R is ethyl can be converted into apovincaminic acid ethyl ester in a single step, by reacting them with ethanol in the presence of an acid (Japanese patent application No. 53-147,100 published Dec. 21, 1978). The compounds of the formula (I) in which $X^1$ is bromine and R is ethyl can be converted into an 11-bromovincamine derivative by subjecting them to deoximation and treating the resulting compound with a base in the presence of an alcohol (German patent application No. 2,928,187 published Jan. 24, 1980). The compounds of the formula (I) in which $X^1$ is bromine are biologically active.

When $X^1$ stands for halogen atom in the compounds of the formula (I), it may represent fluorine, chlorine, bromine or iodine. Of the $C_{1-6}$ alkyl groups represented by R straight-chained and branched alkyl groups, such as the methyl, ethyl, n-propyl, isopropyl, n-butyl, tert.-butyl and isobutyl groups are to be mentioned.

The compounds of the formula (I) in which $X^1$ is hydrogen and R is ethyl were described first in the Hungarian patent specification No. 163,769 as intermediates in the synthesis of biologically active compounds. According to the cited reference these compounds are prepared by subjecting the appropriately substituted 1-methoxycarbonylethyl-octahydroquinolisine to ring closure in the presence of a strong base, such as an alkali hydride or an alkali amide, and nitrosating the resulting oxoeburnane derivative with an alkyl nitrite in the presence of a strong base, such as an alkali hydride.

This method has, however, several disadvantages particularly with regard to large-scale realization. A precondition of the successful reaction with alkali hydrides and alkali amides is the perfect exclusion of water, which involves numerous problems and requires specific care, and may be the source of several deficiencies. The alkyl nitrites utilized in the nitrosation step are detrimental to health, thus specific precautionary measures should be taken during this operation.

The acids which can be used to form the acid addition salts of the compounds having the formula (I) include: mineral acids, such as hydrogen halides (e.g. hydrochloric acid, hydrobromic acid, etc.), sulfuric acid and phosphoric acid, organic carboxylic acids, such as formic acid, acetic acid, propionic acid, oxalic acid, glycolic acid, maleic acid, fumaric acid, succinic acid, tartaric acid, ascorbic acid, citric acid, malic acid, salicyclic acid, lactic acid, benzoic acid and cinnamic acid, alkylsulfonic acids, such as methanesulfonic acid, arylsulfonic acids, such as p-toluenesulfonic acid, furthermore cyclohexylsulfonic acid, aspartic acid, glutamic acid, N-acetylaspartic acid, N-acetylglutamic acid.

Salt formation can be performed in the presence of an inert solvent, such as a $C_{1-6}$ aliphatic alcohol, by dissolving the racemic or optically active base of the formula (I) in said solvent and adding the selected acid or a solution thereof formed with the same solvent to the solution of the base until the mixture becomes slightly acidic (pH about 5-6). Thereafter the separated acid addition salt is isolated from the reaction mixture e.g. by filtration.

The starting substances of the formula (II) in which $X^1$ is hydrogen and R is ethyl and their preparation are described in Tetrahedron 33, 1803 (1977). The derivatives which contain other lower alkyl groups as substituent R can be prepared by the same procedure.

The starting substances of the formula (II) in which $X^1$ is a halogen atom in position 9 or 11 and R stands for a $C_{1-6}$ alkyl group are new compounds and possess valuable biological effects. These compounds can be prepared by halogenating the respective compounds of the formula (II) in which $X^1$ is hydrogen and R is a $C_{1-6}$ alkyl group. Further details of this process are given in our co-pending Hungarian patent application No. RI-721. The compounds of the formula (II) in which $X^1$ is a halogen atom in position 10 and R stands for a $C_{1-6}$ alkyl group can be prepared as described in our co-pending Hungarian patent application No. RI-723 (corresponding to U.S. application Ser. No. 175,383).

The compounds of the formula (II) can be utilized in the process of the invention directly as the mixtures of 15-epimers formed in the above processes, without any purification. One can also subject, however, the crude mixture of 15-epimers first to an epimerization step, which also involves a certain degree of purification, and conduct then the process of the invention with any of the pure epimers.

Epimerization can be performed by recrystallizing the crude mixture of 15-epimers from methanol. This operation also serves as purification, since, beside the undesired epimer, any other contaminants, such as starting substances, intermediates, decomposition products, etc., are removed as well. The solid product of recrystallization is one of the epimers; the other epimer can be separated from the mother liquor by preparative layer chromatography, utilizing silica gel as an adsorbent and a 14:3 mixture of benzene and methanol as eluent.

Racemic and optically active compounds of the formula (II) can equally be used as starting substances in the process of the invention.

When converting the compounds of the formula (II) into the respective 15-halo derivatives of the formula (III), halogenating agents capable of exchanging an alcoholic or phenolic hydroxy group to halogen without simultaneously halogenating the aromatic ring are used. Of these halogenating agents e.g. halides and oxyhalides of phosphorous or sulfur, such as phosphorous oxychloride, phosphorous trichloride, phosphorous pentachloride, thionyl chloride, phosphorous pentabromide, and phosphorous tribromide are to be mentioned.

Halogenation is performed in the presence of an inert organic solvent, preferably in an optionally substituted aromatic hydrocarbon. The preferred solvent is chlorobenzene.

Halogenation is performed at elevated temperatures, preferably at the boiling point of the reaction mixture. Under such conditions the reaction proceeds within some hours, preferably within 1 to 5 hours.

The compounds of the formula (III) obtained in this halogenation step are also mixtures of the respective 15-epimers. It is not necessary to separate the individual epimers from each other in this step, since in the next step of the synthesis the centre of asymmetry in position 15 is eliminated. However, if desired, the individual epimers can be separated from each other by preparative layer chromatography, since they have different $R_f$ values.

The compounds of the formula (III), wherein $X^1$ and R are as defined above and $X^2$ stands for halogen, such as fluorine, chlorine, bromine or iodine, are new substances and possess biological activity. These compounds and their preparation are also embraced by the scope of the invention.

The compounds of the formula (III) are converted into the end-products of the formula (I) by reacting them with an alkali nitrite in the presence of an acid. This reaction can be performed in the presence of a solvent, but the excess of the acid solution can also serve as reaction medium. The alkali nitrite, such as potassium or sodium nitrite, can be introduced as an aqueous solution. The acids usable in this step include organic acids, such as acetic acid, and mineral acids, furthermore aqueous solutions thereof (e.g. 1 n hydrochloric acid solution) are to be mentioned. Water-miscible solvents, such as alcohols, dimethyl formamide, dimethyl sulfoxide, dioxane, tetrahydrofuran, and water-immiscible solvents, such as dichloromethane, can also be used as reaction medium, and the reaction can also be performed in the excess of the acidic solution.

According to a preferred method the compounds of the formula (III) are treated with an aqueous solution of sodium nitrite in acetic acid. The reaction is performed preferably at room temperature.

The above reaction yields the end-products of the formula (I) in the form of the free bases. If desired, the free bases can be converted into their acid addition salts utilizing the organic or mineral acids listed above. The salts are generally crystalline solids, easy to identify.

If desired, the compounds of the formula (I) can be subjected to further purification steps, such as recrystallization from an appropriately selected solvent. As solvent a dialkyl ether, such as diethyl ether, can be used.

If desired, the racemic compounds of the general formula (I) can be resolved by methods known per se.

Both the intermediates and the end-products can be prepared according to the invention in forms easy to identify. The analytical date, IR spectra and mass spectra of the compounds prepared are in harmony with the assigned structures.

The invention is elucidated in detail with the aid of the following non-limiting Examples.

EXAMPLE 1

(+)-3(S),17(S)-14-Oxo-15-chloro-E-homoeburnane (mixture of 15-epimers)

A mixture of 4.20 g (13 mmoles) of (+)-3(S),17(S)-14-oxo-15-hydroxy-E-homoeburnane (mixture of 15-epimers), 100 ml of chlorobenzene and 4.2 g of phosphorous oxychloride is stirred and refluxed for 3 hours. The reaction mixture is cooled, diluted with 100 g of ice water under stirring, and the pH of the resulting mixture is adjusted to 8.5 with 5% aqueous sodium carbonate solution. The mixture is poured into a separatory funnel, shaken well, and the phases are allowed to separate. The lower phase is separated, and the upper aqueous phase is extracted twice with 50 ml of dichloromethane, each. The organic solutions are combined, dried over magnesium sulfate, filtered, and the filtrate is evaporated to dryness in vacuo. 3.50 g of the named compound are obtained as a residue. This substance can be introduced into the next step of the synthesis without any purification.

Yield: 81%; m.p.: 140°–152° C.

When subjecting the crude product to preparative layer chromatography (adsorbent: KG-PF$_{254+356}$ grade silica gel, solvent: a 14:3 mixture of benzene and methanol, eluting agent: acetone), two stereoisomeric chlorine compounds can be separated.

The isomer with the higher $R_f$ value melts at 155° C. (after recrystallization from methanol). IR (KBr): 1700 cm$^{-1}$ (lactam CO).

Mass spectrum: m/e (%): 342 (M+, 100), 279 (26), 252 (37), 251 (21), 250 (17), 249 (48), 237 (13), 223 (13), 194 (16), 180 (27), 169 (27).

The isomer with the lower $R_f$ value melts at 142° C. (after recrystallization from methanol). IR (KBr): 1720 cm$^{-1}$ (lactam CO).

Mass spectrum: m/e (%): 342 (M+, 71), 307 (63), 308 (100), 280 (22), 252 (45), 249 (34), 223 (18), 169 (20).

$[\alpha]_D^{20} = +63.3°$ (c=1.01%, in chloroform).

EXAMPLE 2

(+)-3(S),17(S)-14-Oxo-15-hydroxyimino-E-homoeburnane 0.20 g (0.58 mmoles) of (+)-3(S),17(S)-14-oxo-15-chloro-E-homoeburnane (a mixture of 15-epimers, prepared as described in Example 1) are dissolved in 4 ml of acetic acid. The solution is diluted with 1 ml of water, and a solution of 1.2 g of sodium nitrite in 4 ml of water is added dropwise to the stirred mixture at room temperature. The resulting solution is allowed to stand at room temperature for 24 hours. Thereafter the pH of the mixture is adjusted to 9 with concentrated aqueous ammonia under ice cooling, and the resulting alkaline mixture is extracted thrice with 5 ml of dichloromethane, each. The dichloromethane solutions are combined, dried over anhydrous magnesium sulfate, filtered, and the filtrate is evaporated to dryness in vacuo. The oily residue, weighing 0.19 g, is purified by preparative layer chromatography (adsorbent: KG-PF$_{254+366}$ grade silica gel, solvent: a 14:3 mixture of benzene and methanol, eluting agent: a 20:5 mixture of dichloromethane and methanol). The $R_f$ value of the starting substance is higher than that of the named compound. The eluate is evaporated to obtain 0.13 g (68%) of the named compound; m.p.: 190° C. (after recrystallization from ether). $[\alpha]_D^{20} = +61°$ (c=1%, in dichloromethane).

IR (KBr): 3200 (OH), 1705 (lactam CO), 1642 (C=N) cm$^{-1}$.

Analysis: calculated for C$_{20}$H$_{23}$N$_3$O$_2$(mol. wt.: 337.4): C: 71.19%, H: 6.87%, N:12.45%; found: C: 71.30%, H: 6.60%, N: 12.65%.

To prepare the hydrochloride the 0.13 g of the free base obtained as described above are dissolved in 1 ml of methanol, the solution is acidified to pH 5 with methanolic hydrochloric acid, the separated salt is filtered off and dried. 0.13 g of the hydrochloride are obtained; m.p.: 256°-257° C. (after recrystallization from methanol).

EXAMPLE 3

(+)-3(S),17(S)-11-Bromo-14-oxo-15-chloro-E-homoeburnane (mixture of 15-epimers)

A solution of 0.85 g of phosphorous oxychloride in 1 ml of chlorobenzene is added to a stirred solution of 1.00 g (2.48 mmoles) of (+)-3(S),17(S)-11-bromo-14-oxo-15-hydroxy-E-homoeburnane (mixture of 15-epimers) in 19 ml of chlorobenzene, and the resulting mixture is refluxed for 2 hours. The reaction mixture is shaken with 15 ml of a 5% aqueous sodium carbonate solution under ice cooling, and the lower organic phase is separated. The aqueous alkaline phase is extracted thrice with 10 ml of a 99:1 mixture of dichloromethane and methanol, each. The organic phases are combined, dried over anhydrous magnesium sulfate, filtered, and the filtrate is evaporated to dryness in vacuo. The resulting 1.00 g of oily substance, which is a mixture of 15-epimers, can be used in the next step of the synthesis without purification.

The mixture of 15-epimers can be subjected to preparative layer chromatography (adsorbent: KG-PF$_{254+366}$ grade silica gel, solvent: a 14:3 mixture of benzene and methanol, eluting agent: a 2:1 mixture of acetone and dichloromethane) to separate the individual isomers.

0.32 g (30.5%) of an isomer with lower $R_f$ value (isomer "A") are obtained; m.p.: 215°-126° C. (after recrystallization from acetone).

IR (KBr): 1705 cm$^{-1}$ (lactam CO).

Analysis: calculated for C$_{20}$H$_{22}$N$_2$OBrCl (mol.wt.: 421.77): C: 56.95%, N: 6.64%, H: 5.25%; found: C: 56.70%, N: 6.45%, H: 5.35%.

$[\alpha]_D^{25} = +55.6°$ (c=1.024%, in chloroform).

The separation yields 0.45 g (43%) of the isomer with higher $R_f$ value (isomer "B") as an oily substance. This substance is treated with methanolic hydrochloric acid, and the resulting hydrochloride is crystallized from acetone. The hydrochloride melts at 269° C. under decomposition.

IR (KBr): 1705 cm$^{-1}$ (lactam CO).

Analysis: calculated for C$_{20}$H$_{23}$N$_2$OBrCl$_2$ (mol.wt.: 458.23): C: 52.41%, H: 5.05%, N: 6.11%; found: C: 52.34%, H: 5.27%, N: 6.20%.

$[\alpha]_D^{25} = 0°$ (c=1.05%, in dichloromethane).

EXAMPLE 4

(+)-3(S),17(S)-11-Bromo-14-oxo-15-hydroxyimino-E-homoeburnane 0.50 g (1.18 mmoles) of (+)-3(S), 17(S)-11-bromo-14-oxo-15-chloro-E-homoeburnane (mixture of 15-epimers, prepared as described in Example 3) are dissolved in 11 ml of glacial acetic acid, a solution of 2.70 g of sodium nitrite in 9 ml of water is added dropwise to the stirred mixture at room temperature, and the resulting mixture is allowed to stand at room temperature for 30 hours. Thereafter the mixture is poured into 20 g of ice water, the pH of the mixture is adjusted to 9 with concentrated aqueous ammonia, and the alkaline solution is extracted thrice with 10 ml of dichloromethane, each. The organic phase is separated, dried over anhydrous magnesium sulfate, filtered, and the filtrate is evaporated. The oily residue, weighing 0.50 g, is purified by preparative layer chromatography (adsorbent: KG-PF$_{254+366}$ grade silica gel, solvent: a 14:3 mixture of benzene and methanol, eluting agent: a 20:4 mixture of dichloromethane and methanol). The $R_f$ value of the starting substance is higher than that of the end-product.

0.32 g (60.5%) of the named compound are obtained as an oily substance. This substance is treated with methanolic hydrochloric acid to obtain the respective hydrochloride as a crystalline solid melting at 235°-236° C. (from methanol).

IR (KBr): 3460 (OH), 1710 (lactam CO), 1622 (C=N) cm$^{-1}$.

Mass spectrum: m/e (%): 415 (M+, 62).

$[\alpha]_D^{25} = +44.9°$ (c=1.10%, in dimethyl formamide).

What we claim is:

1. A compound of the formula (III)

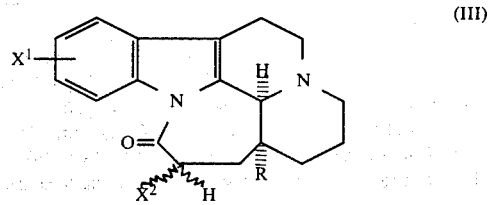

(III)

wherein

X$^1$ is hydrogen or halogen,

R is $C_1$ to $C_6$ alkyl, and
$X^2$ is halogen, or a 15-epimer or a pharmaceutically acceptable acid addition salt thereof.

2. (+)-3(S),17(S)-11-bromo-14-oxo-15-chloro-E-homoeburnane or a 15-epimer thereof.

3. A process for the preparation of a compound of the formula (I)

(I) [structure]

wherein
$X^1$ is hydrogen or halogen, and
R is $C_1$ to $C_6$ alkyl,
or a pharmaceutically acceptable acid additon salt thereof which comprises the steps of:
(a) halogenating a compound of the formula (II)

(II) [structure]

or a 15-epimer of a pharmaceutically acceptable acid addition salt thereof, to produce a compound of the formula (III)

(III) [structure]

or a 14-epimer of a pharmaceutically acceptable acid addition salt thereof wherein $X^2$ is halogen;
(b) oximating the compound of the formula (III) with an alkali nitrite in the presence of an acid to prepare the compoundd of the formula (I); and
(c) in the case where a pharmaceutically acceptable acid addition salt of the compound of the formula (I) is prepared, converting the compound of formula (I) to a pharmaceutically acceptable acid addition salt.

4. The process defined in claim 3, step (a), wherein the compound of the formula (II) is halogenated with a halogenating agent selected from the group consisting of a phosphorous halide and a phosphorous oxyhalide.

5. The process defined in claim 3, step (a), wherein the halogenation is performed in an inert organic solvent.

6. The process defined in claim 5, wherein the inert organic solvent is a hydrocarbon or a chlorohydrocarbon.

7. The process defined in claim 3, step (b), wherein the alkali nitrite is sodium nitrite.

8. The process defined in claim 3, step (b), wherein the acid is acetic acid.

9. The process defined in claim 3 wherein prior to step (a), the individual 15-epimers of the compound of the formula (II) are separated from one another.

10. The process defined in claim 3 wherein prior to step (a), the compound of the formula (II) is resolved.

11. The process defined in claim 3 wherein prior to step (b), the individual 15-epimers of the compound of the formula (III) are separated from one another.

12. The process defined in claim 3 wherein prior to step (b), the compound of the formula (III) is resolved.

13. The process defined in claim 3 which further comprises resolving the compound of formula (I).

14. A process for the preparation of a compound of the formula (I)

(I) [structure]

wherein
$X^1$ is hydrogen or halogen, and
R is $C_1$ to $C_6$ alkyl, or
a pharmaceutically acceptable acid addition salt thereof which comprises the steps of:
(a) oximating a compound of the formula (III)

(III) [structure]

wherein $X^2$ is halogen or a 15-epimer thereof with an alkali nitrite in the presence of an acid to prepare the compound of the formula (I); and
(b) in the case where a pharmaceutically acceptable acid addition salt of the compound of the formula (I) is to be prepared, converting the compound of the formula (I) to a pharmaceutically acceptable acid addition salt.

15. The process defined in claim 14, step (a), wherein the alkali nitrite is sodium nitrite.

16. The process defined in claim 14, step (a), wherein the acid is acetic acid.

17. The process defined in claim 14 wherein prior to step (a), the individual 15-epimers of the compound of the formula (III) are separated from one another.

18. The process defined in claim 14 wherein prior to step (a), the compound of the formula (III) is resolved.

19. The process defined in claim 14 wherein the compound of the formula (I) formed during step (a) is resolved.

20. A process for the preparation of a compound of the formula (III)

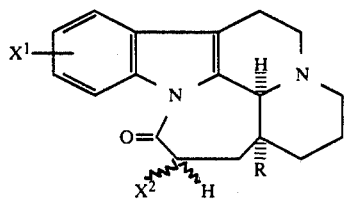

(III)

wherein $X^1$ is hydrogen or halogen,

R is $C_1$ to $C_6$ alkyl, and $X^2$ is halogen, or a 15-epimer or pharmaceutically acceptable acid addition salt thereof which comprises the steps of:

(a) halogenating a compound of the formula (II)

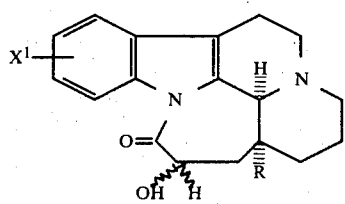

(II)

to produce a compound of the formula (III) or a 15-epimer thereof; and (b) in the case where a pharmaceutically acceptable acid addition salt of the compound of the formula (III) is to be prepared, converting the compound of the formula (III) to a pharmaceutically acceptable acid addition salt.

21. The process defined in claim 20, step (a), wherein the compound of the formula (II) is halogenated with a halogenating agent selected from the group consisting of a phosphorous halide and a phosphorous oxyhalide.

22. The process defined in claim 21, step (a) wherein the halogenation is performed in an inert organic solvent.

23. The proces defined in claim 22, wherein the inert organic solvent is a hydrocarbon or a chlorohydrocarbon.

24. The process defined in claim 22 wherein prior to step (a), the individual 15-epimers of the compound of the formula (II) are separated from one another.

25. The process defined in claim 22 wherein prior to step (a), the compound of the formula (II) is resolved.

26. The process defined in claim 22 wherein following step (a), the individual 15-epimers of the compound of the formula (III) are separated from one another.

27. The process defined in claim 22 wherein following step (a), the compound of the formula (III) is resolved.

* * * * *